(12) United States Patent
Furnish

(10) Patent No.: US 8,386,023 B2
(45) Date of Patent: Feb. 26, 2013

(54) CATHETER PROBE ARRANGEMENT FOR TISSUE ANALYSIS BY RADIANT ENERGY DELIVERY AND RADIANT ENERGY COLLECTION

(75) Inventor: Simon M. Furnish, New York, NY (US)

(73) Assignee: InfraReDx, Inc., Burlington, MA (US)

( * ) Notice: Subject to any disclaimer, the term of this patent is extended or adjusted under 35 U.S.C. 154(b) by 0 days.

(21) Appl. No.: 13/084,418

(22) Filed: Apr. 11, 2011

(65) Prior Publication Data

US 2011/0230770 A1    Sep. 22, 2011

Related U.S. Application Data

(63) Continuation of application No. 10/037,306, filed on Dec. 31, 2001, now abandoned.

(51) Int. Cl.
*A61B 5/00* (2006.01)

(52) U.S. Cl. ............ 600/478; 600/476; 606/13; 606/15; 606/16; 606/17; 385/115; 385/117; 385/119

(58) Field of Classification Search ................... 600/407, 600/476, 478; 606/13–18; 385/60, 73, 74, 385/115, 117, 119
See application file for complete search history.

(56) References Cited

U.S. PATENT DOCUMENTS

| | | | |
|---|---|---|---|
| 4,195,904 A | 4/1980 | Yamashita | |
| 4,672,961 A | 6/1987 | Davies | |
| 4,832,023 A | 5/1989 | Murphy-Chutorian et al. | |
| 4,850,351 A | 7/1989 | Herman et al. | |
| 4,887,605 A | 12/1989 | Angelsen et al. | 600/439 |
| 4,917,097 A | 4/1990 | Proudian et al. | |
| 4,950,266 A | 8/1990 | Sinofsky | |
| 4,967,745 A | 11/1990 | Hayes et al. | |
| 5,081,993 A | 1/1992 | Kitney et al. | |
| 5,242,438 A | 9/1993 | Saadatmanesh et al. | |
| 5,405,318 A | 4/1995 | Nita | |
| 5,456,259 A | 10/1995 | Barlow et al. | |
| 5,458,126 A | 10/1995 | Cline et al. | 600/425 |
| 5,465,726 A | 11/1995 | Dickinson et al. | |
| 5,470,330 A | 11/1995 | Goldenberg et al. | |

(Continued)

FOREIGN PATENT DOCUMENTS

| | | |
|---|---|---|
| DE | 4326037 | 9/1995 |
| EP | 0947221 | 6/1999 |

(Continued)

OTHER PUBLICATIONS

Notice of Reasons for Rejection dated Jan. 6, 2010 for Japanese Patent Application No. 2004-569174 with English Translation. 5 Pages.

(Continued)

*Primary Examiner* — Ruth S Smith
(74) *Attorney, Agent, or Firm* — Rothwell, Figg, Ernst & Manbeck PC

(57) ABSTRACT

A catheter tip apparatus arranged in a catheter for the delivery and collection of a light-energy signal to permit subsequent computerized analysis of body tissue by the collected signal. The apparatus comprises an elongated housing supporting a first reflective surface and a second reflective surface. The first reflective surface and the second reflective surface are longitudinally spaced apart from one another. A first flexible, elongated energy bearing delivery fiber has a distalmost end arranged adjacent the first reflective surface. A second flexible, elongated energy bearing collection fiber has a distalmost end arranged adjacent the second reflective surface. The housing is rotatably supported on a flexible catheter sheath for insertion of the catheter into a mammalian body for tissue analysis thereof.

10 Claims, 9 Drawing Sheets

U.S. PATENT DOCUMENTS

| | | | |
|---|---|---|---|
| 5,582,170 A | 12/1996 | Soller | 600/322 |
| 5,700,243 A | 12/1997 | Narciso, Jr. | |
| 5,716,320 A | 2/1998 | Buttermore | |
| 5,730,700 A | 3/1998 | Walther et al. | 600/104 |
| 5,827,267 A | 10/1998 | Savage et al. | |
| 5,830,209 A | 11/1998 | Savage et al. | |
| 5,836,941 A | 11/1998 | Yoshihara et al. | |
| 5,876,345 A | 3/1999 | Eaton et al. | |
| 5,953,477 A | 9/1999 | Wach et al. | |
| 6,026,316 A | 2/2000 | Kucharczyk et al. | |
| 6,148,095 A | 11/2000 | Prause et al. | 382/131 |
| 6,156,029 A | 12/2000 | Mueller | |
| 6,270,492 B1 | 8/2001 | Sinofsky | |
| 6,283,921 B1 | 9/2001 | Nix et al. | |
| 6,289,232 B1 | 9/2001 | Jakob et al. | 600/410 |
| 6,321,106 B1 | 11/2001 | Lemelson | |
| 6,416,234 B1 | 7/2002 | Wach et al. | |
| 6,473,636 B1 | 10/2002 | Wei et al. | 600/436 |
| 6,485,413 B1 | 11/2002 | Boppart et al. | 600/160 |
| 6,490,382 B1 * | 12/2002 | Hill | 385/17 |
| 6,511,475 B1 | 1/2003 | Altshuler et al. | |
| 6,577,891 B1 | 6/2003 | Jaross et al. | 600/473 |
| 6,678,541 B1 * | 1/2004 | Durkin et al. | 600/310 |
| 2002/0183622 A1 | 12/2002 | Zuluaga et al. | |
| 2002/0183623 A1 | 12/2002 | Tang et al. | |
| 2003/0100824 A1 | 5/2003 | Warren et al. | |

FOREIGN PATENT DOCUMENTS

| | | |
|---|---|---|
| EP | 1075821 | 2/2001 |
| JP | 219018 | 2/1990 |
| JP | 05103774 A | 4/1993 |
| JP | 10311954 A | 11/1998 |
| JP | 11276499 A | 10/1999 |
| JP | 2000-515407 A | 11/2000 |
| JP | 200179007 A | 3/2001 |
| JP | 2002263106 A | 9/2002 |
| WO | 9805253 | 2/1998 |

OTHER PUBLICATIONS

Notice of Reasons for Rejection dated Jan. 7, 2009 for Japanese Patent Application No. 2004-569174 with English Translation. 7 Paages.

Barber et al., "Ultrasonic Duplex Echo-Doppler Scanner," *IEEE Transactions on Biomedical Engineering*, vol. BME-21, No. 2, pp. 109-113 (Mar. 1974).

Bow et al., "Cardiac Imaging with a Real-Time Ultrasonic Scanner of a Rotating Transducer Design," *Proceedings of the British Medical Ultrasound Society*, p. 645 (Aug. 1978).

"Coronary-Artery Bypass Surgery," *The Lancet*, pp. 264-265 (Feb. 4, 1978).

Hisanaga et al., "High Speed Rotating Scanner for Transesophageal Cross-Sectional Echocardiography," *The American Journal of Cardiology*, vol. 46, pp. 837-842 (Nov. 1980).

Lancée et al., "Construction of a circular ultrasonic array with miniature elements for cardiac application," Thorax Center, Department of Echocardiography and Central Research Workshop, Erasmus University, Rotterdam, The Netherlands, pp. 49-53 (undated).

Martin et al., "An Ultrasonic Catheter Tip Instrument for Measuring Volume Blood Flow," Departments of Anesthesiology & Bioengineering, University of Washington, Seattle, Washington, pp. 13-17 (undated).

Martin et al., "Ultrasonic Catheter Tip Instrument for Measurement of Vessel, Cross-Sectional Area," 27$^{th}$ ACEMB, Marriott Hotel, Philadelphia, Pennsylvania, p. 186 (Oct. 6-10, 1974).

Martin and Watkins, "An Ultrasonic Catheter for Intravascular Measurement of Blood Flow: Technical Details," *IEEE Transactions on Sonics and Ultrasonics*, vol. SU-27, No. 6, pp. 277-286 (Nov. 1980).

Pérez et al., "Applicability of Ultrasonic Tissue Characterization for Longitudinal Assessment and Differentiation of Calcification and Fibrosis in Cardiomyopathy," *American College of Cardiology*, vol. 4, No. 1, pp. 88-93 (Jul. 1984).

Tomoike et al., "Continuous measurement of coronary artery diameter in situ," *American Physiological Society*, pp. H73-H79 (undated).

Van Orden et al., "A technique for monitoring blood flow changes with miniaturized Doppler flow probes," *American Physiological Society*, pp. H1005-H1009 (undated).

Ycas and Barnes, "An Ultrasonic Drill for Cleaning Blood Vessels," Department of Electrical Engineering, University of Colorado, Boulder, Colorado, pp. 165-167 (undated).

* cited by examiner

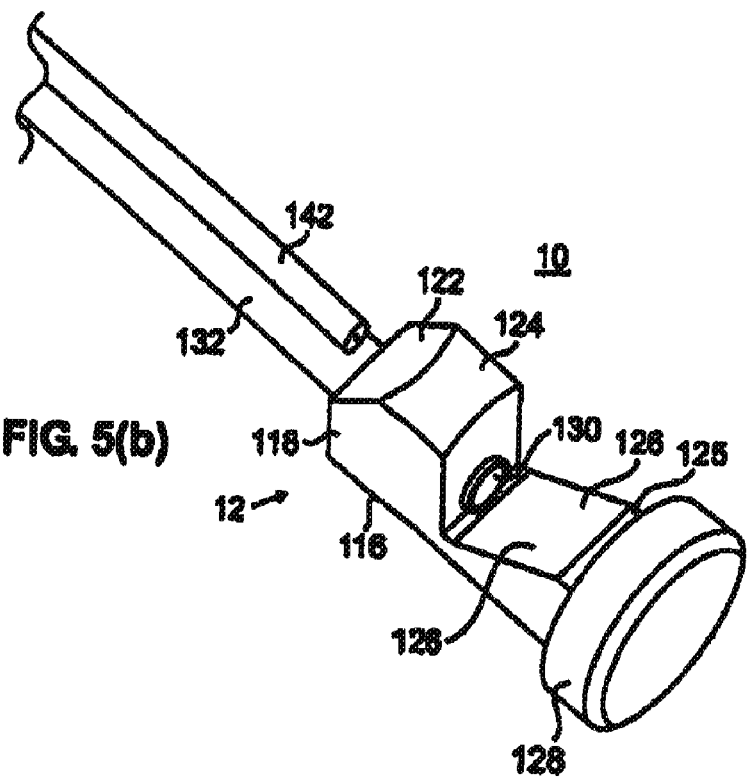
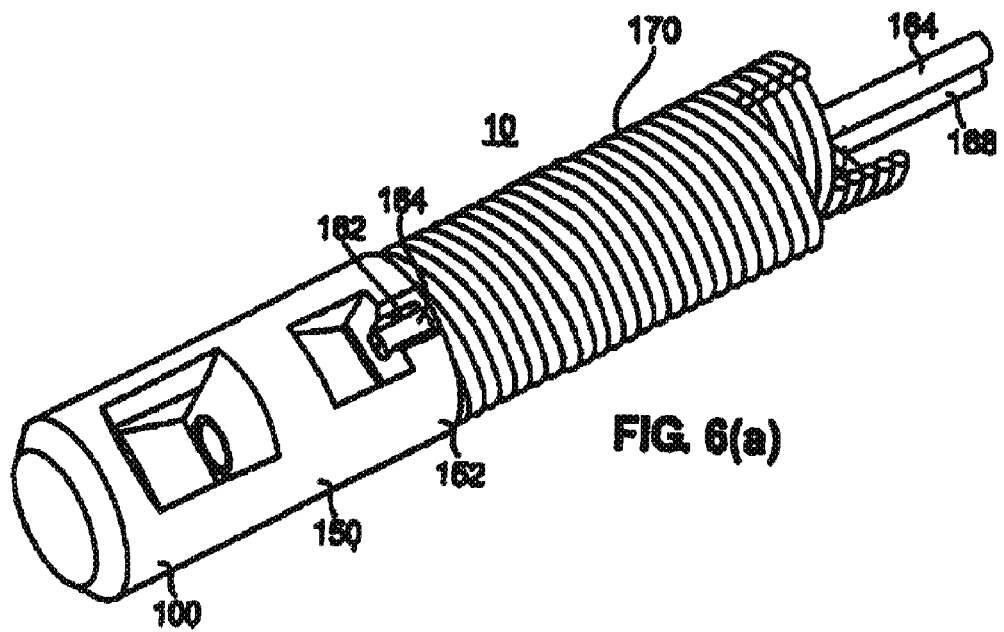

CATHETER PROBE ARRANGEMENT FOR TISSUE ANALYSIS BY RADIANT ENERGY DELIVERY AND RADIANT ENERGY COLLECTION

CROSS REFERENCE TO RELATED APPLICATIONS

This application is a continuation of U.S. patent application Ser. No. 10/037,306, filed Dec. 31, 2001 now abandoned, the disclosure of which is incorporated herein in its entirety by reference.

BACKGROUND OF THE INVENTION

1. Field of the Invention

This application relates to photo-medical devices, and more particularly

This application relates to photo-medical devices, and more particularly to photo-medical devices that deliver and collect radiant energy to permit body tissue analysis and/or treatment, and is a continuation of patent application, Ser. No. 10/037,306 filed on Dec. 31, 2001, entitled "Multi-Fiber Catheter Probe Arrangement for Tissue Analysis or Treatment," now abandoned, which is incorporated herein by reference in its entirety.

2. Prior Art

The sensing and treating of various tissue characteristics in the in vivo intravascular environment is desirous for many reasons yet difficult because it is a very harsh environment in which to conduct such analysis or treatment. The presence of blood and its constituents such as cholesterol may effect scattering and absorption of energy signals transmitted within an organ. Diagnosis and treatment of various tissues within the human body using an in vivo probe necessitates adaptive characteristics for that probe when it is inserted into a mammalian body organ.

It is an object of the present invention to provide a probe for insertion within a mammalian body which overcomes the disadvantages of the prior art.

It is a further object of the present invention to provide a minimally invasive device for light energy transmitting (i.e. infrared through ultraviolet) diagnosis and treatment of mammalian tissue through the use of endoscopes, catheters and other minimally invasive devices.

It is still yet a further object of the present invention to provide optical probe tip arrangement which facilitates optimum delivery and retrieval of energy signals within the human body tissue.

BRIEF SUMMARY OF THE INVENTION

The present invention provides several preferred embodiments of apparatus and of method of use of that apparatus to analyze body tissue using an energy spectrum analysis distributed and received by an elongated probe introducable through a catheter into that body tissue. That introduction of the body probe may be done through an endoscope, or other catheter-like devices for such energy diagnosis and treatment of tissue. That energy analysis and treatment may include near infrared (NIR) reflectance spectroscopy, Raman spectroscopy, fluorescence spectroscopy, photodynamic drug activation, photonic ablation or thermal treatments, and optical coherence tomography.

The probe of the present invention comprises an elongated, generally cylindrically shaped housing having a first or distal end and a second, or proximal end. The proximal end has a stem thereon of reduced diameter from the diameter of the distalmost portion thereof. An elongated groove is arranged to extend from the proximal end of the stem through towards the distal end of the housing. The groove is disposed through only one side of the housing, and has an arrangement of angled shoulders therein for providing snug receipt of the collector and the delivery fiber arrangement.

The collector fiber arrangement in this particular embodiment includes an elongated flexible collection fiber having a distal end to which a reflector or reflective surface (i.e., a mirror member) is attached. The collection fiber has an outer buffer such as a sheath for protection of the fiber and to minimize stray radiation therefrom. A mirror member has an angularly disposed reflective surface thereon. The delivery reflector (or mirror member) is attached to an optical delivery fiber which is enclosed similarly by an outer buffer such as a sheath for protection of the fiber and for minimization of light leakage. The delivery reflector or mirror member has an angled reflective surface thereon. The collection fiber and reflector and the delivery fiber and reflector jointly mate within the elongated receiving groove within the stem and tip housing. The elongated groove is preferably shaped to effect accurate positioning of the respective reflectors or mirror members therein, so as to emit radiation from the delivery reflector (or mirror member) and receive radiation reflected back from a body tissue sample in the collection reflector (or mirror member). Once the collection and delivery fibers are within the housing, those joint fibers may be inserted within an elongated catheter shaft or rotatable coil as will be described hereinbelow.

A further embodiment of the present invention is disclosed by a elongated support frame having a proximal end and a distal end. The proximal end includes and upstanding portion through which a collection fiber channel is arranged (i.e., molded, drilled, machined). A rectilinearly-shaped holding pocket is arranged distal of the first upstanding member and is arranged to receive a reflective mirrored surface for example, a collection prism, thereon. A midblock portion is arranged centrally in the support frame and has a delivery fiber channel arranged therewithin, the delivery fiber channel extending parallel and adjacent the collection fiber channel. A second holding pocket is similarly arranged adjacent the delivery fiber channel for receipt of a second reflector such as a reflective mirrored surface, such as for example, a mirror member, having a mirrored surface thereon. The holding pockets are constructed so as to accurately receive and align the respective first and second mirror members to the desired angle for the desired photon delivery and photon collection from a target body tissue. The elongated support frame is arranged within an elongated housing, having an elongated channel for receipt thereof. A delivery fiber and a collection fiber would be inserted within their respective channels and the respective reflectors (i.e. mirror members) would be secured (i.e. affixed by adhesive) within their respective holding pockets.

A further embodiment of the optical probe arrangement of the present invention is characterized by a generally cylindrically shaped frame member having a stepped down stem portion on its proximal end thereof. The frame member is arranged so as to define a series of distal step portions, the first portion of which is arranged to receive a collection reflector (i.e. mirror member or reflective surface) and second stepped portion receives a delivery reflector (i.e. mirror member or reflective surface). A bore or channel is arranged through the frame member for servicing each particular reflector. Each respective channel receives an optical fiber which is arranged to abut one surface of its respective reflector. The distal cover may be arranged so as to mate over the respective collection reflector and the delivery reflector while having a slot for passage of a photonic signal therethrough. The delivery reflector is thus permitted to emit photonic radiation and the collection reflector is permitted to receive photonic radiation when the frame member is assembled with the cover, and the stem is attached in holding the particular fiber, and those fibers are inserted within a hollow torqueable transmission shaft such as a counterwound, multifilar drive shaft coil arrangement proximal of that frame member.

A further embodiment of the probe arrangement is shown by an elongated frame member having a proximal end and a distal end. The proximal end of that frame member is arranged so as to define an angled reflective surface thereat, the distal end of that frame member having a second reflective surface angularly disposed thereon with an oval end cap thereon. A bore is arranged through the proximal end of the elongated frame member to define a receiving channel for a delivery fiber to be inserted therewithin. The entire elongated frame member is inserted into an elongated cylindrically shaped housing having a proximal end and a distal end. The proximal end of the housing has a stem of stepped down diameter, which stem encloses an energy delivery fiber and an energy collection fiber. The stem of the housing is arranged to receive the collection fiber which is arranged to receive reflective signals from its reflector surface arranged onto the elongated frame member. The housing has an opening arranged longitudinally therein, so as to receive the elongated frame member. The housing also has a slot cut through a side portion thereof so as to permit the energy signal to be delivered and received by the respective reflective surfaces contained therewithin. The end cap on the distalmost end of the elongated frame member abuts the distalmost end of the elongated housing to define a smooth continuous surface therearound.

A further embodiment of the present invention resides in a one piece housing of generally cylindrical shape having a proximal portion of stepped down diameter defining a stem. A first reflective collection surface is disposed at a particularly desired angle adjacent the stem of the elongated housing, and a second reflective surface is arranged into the elongated housing adjacent its distalmost end. A first bore is arranged through the housing through the stem so as to receive a collection fiber. A second bore is also arranged through the elongated housing so as to support a delivery fiber therethrough. The stem may be received in a pair of hollow, flexible, counterwound coils which function as a torqueable transmission shaft which is secured to the stem and surrounds the delivery and collection fibers received therethrough. The first and second reflective surfaces arranged in the housing, in this embodiment, may be skewed (non-parallel or curvilinear) so as to emit and receive signals from any particular direction with respect to its adjacent reflective surface.

A yet further embodiment of the present invention relates to a method of constructing a catheter tip arrangement for support of a plurality of optical fibers, which support construction permits minimization of component size and adaptive angularity of reflection of the delivery and collection beams. Such a support may be accomplished by micromachining construction where additive processing such as for example: plating, sputtering, vapor deposition, and subtractive processing such as for example: etching, laser cutting and ablation, permits finite adjustment to the dimensions. The support comprises a base upon which an arrangement of parallel bosses are "grown", the bosses defining between them, a pair of parallel slots into which a delivery and a collection fiber may be mated. A mirror surface and support struts are spaced at the distalmost location of the fibers, which mirror surface may be curved or manipulably bent to the desired angle for maximizing optical analysis and tissue treatment thereby. This embodiment contemplates the use of index-matching fluids added to any gap between a catheter sheath surrounding the fibers to reduce any back reflections from the interior of the protective sheath/transmission window.

The invention thus comprises a catheter tip apparatus arranged in a catheter for the delivery and collection of a light energy signal to permit subsequent computerized analysis of body tissue by the collected signal. The apparatus comprises an elongated housing member supporting a first reflective surface and a second reflective surface. The first reflective surface and the second reflective surface are longitudinally spaced apart from one another. A first flexible, elongated, light energy bearing delivery fiber has a distalmost end arranged adjacent the first reflective surface. A second flexible, elongated energy bearing collection fiber has a distalmost end arranged adjacent the second reflective surface. The housing member is rotatably supported on a flexible catheter sheath for insertion of the catheter into a mammalian body for tissue analysis thereof. The housing may comprise a frame member having a slot arranged therein for receipt and alignment of the first and the second reflective surfaces. The first and the second reflective surfaces may comprise prism members. The slot may have shoulders therein to secure and accurately align the reflective surfaces therein. The housing may have a proximalmost stem portion for receipt into a catheter sheath to permit manipulation of the tip from a proximal location. The housing may be comprised of a frame member having a proximal end and a distal end, with an upstanding proximal block and an upstanding midblock, each block having a holding pocket thereadjacent for receipt of a reflective surface attachable therein. The reflective surface may comprise a prism fixedly attached into the pocket. Each of the upstanding blocks may have a bore therethrough for receipt of one of the energy bearing fibers. The housing may comprise an elongated generally cylindrically shaped frame member with a proximal end and a distal end, the frame member having at least two steps thereon of decreasing thickness in the distal direction, each of the steps having a reflective surface mounted thereon, the proximal end having a stem portion of reduced diameter, to permit rotative receipt within a tubular catheter sheath. The frame member may have a cover member arranged to mate over the steps and the reflective surfaces of the housing. The cover member may have an axially arranged slot thereon through part of its longitudinal length, the slot being disposed radially adjacent each of the reflective surfaces to permit delivery and reflected collection of an energy beam therethrough. The stem portion may be secured to a multi-layered, elongated coil spring arrangement to permit twisting control of the catheter tip within a mammalian body component. The reflective surfaces may be unitary portions of the housing. The housing has a proximal end and a distal end, and the proximal end may mate with a housing enclosure, the enclosure providing a securement means for the energy collecting fiber and the housing providing a securement means for the energy delivery fiber. The housing enclosure attached to said proximal end of said housing may have a longitudinally directed elongated slot therein, the slot being in radial alignment with the reflective surfaces formed on the housing to permit transmission and collection of radiant energy via the respective reflective surfaces to a computerized analysis system. The housing may comprise a cylindrically shaped member having its first and second reflective surfaces machined thereon, and wherein the first and second reflective surfaces are non-parallel with respect to one another. The first and second fibers may be diametrically oppositely arranged with respect to the longitudinal axis of rotation of the housing, to minimize any undesired motion of the housing during its rotation in a body tissue. The housing may include a reflective surface which is bendable to effect directional change of an energy beam reflecting therefrom. The housing may be made of "accumulation" or "deletion" components defining a fiber alignment slot for miniaturization of the tip.

The present invention also comprises a catheter tip apparatus arranged in a catheter for the delivery and collection of an energy signal to permit subsequent computerized analysis of body tissue by the collected signal. The apparatus comprises an elongated housing having a longitudinal axis of rotation, the housing having a first reflective surface disposed thereon, a second reflective surface disposed on the housing distally of the first reflective surface and in axial alignment therewith; and a first light conductive fiber in light coupled communication with the first reflective surface and a second light conductive fiber in light coupled communication with the second reflective surface, the first light conductive fiber in communication being in communication with a controlled analytical-light generating source and the second light conductive fiber being in communication with a light-collection analysis device. The first reflective surface may be dimensionally larger than the second reflective surface. The first reflective surface may be curvilinear. The first reflective surface may be non-parallel with respect to the second reflective surface. At least one of the first and second reflective surfaces may be spaced apart from the light conductive fibers. The first reflective surface may be disposed radially within and spaced from the perimeter of the housing to permit a spreading of a light beam from the first reflective surface onto the body tissue. An index matching fluid may be arranged between a distal end of the conductive fiber and the reflective surface. The reflective surface may be positioned in a holding pocket arranged in the housing. The reflective surface may be comprised of a mirrored surface. The holding pocket may be utilized to align the reflective surface with respect to the housing. The conductive light fibers may be each individually arranged within a bore disposed within the housing. The light delivery fibers may be equally diametrically opposed about the axis of rotation of the housing to provide balance thereto and minimize eccentricity during rotation thereof.

The invention may also comprise a catheter tip apparatus arranged in a catheter for the delivery and collection of an energy signal to permit subsequent computerized analysis of body tissue by the collected signal, the apparatus comprising an elongated housing having a longitudinal axis of rotation, the housing having a first reflective surface disposed thereon, a second reflective surface disposed on the housing distally of the first reflective surface and in axial alignment therewith. A first light conductive fiber may be in light-coupled communication with the first reflective surface and a second light conductive fiber in light-coupled communication with the second reflective surface, the first light conductive fiber in communication being in communication with a controlled analytical-light generating source and the second light conductive fiber being in communication with a light-collection analysis device. A curvilinear cover may be arranged to mate over a distal portion of the housing to enclose the reflective surfaces, the cover having at least one opening on an annular surface thereof to permit light delivery to the body tissue, and to permit light collection therethrough upon reflection from the body tissue. At least one of the reflective surfaces may comprise a mirror or polished surface. Each of the light conductive fibers has a distal end arranged within said housing, and the at least one of the light conductive fibers is in abutting relationship with a non-reflective surface of the member containing the reflective surface. At least one of the reflective surfaces may be disposed in a holding pocket. The reflective surface may be secured in the holding pocket by an adhesive.

The invention also comprises a catheter tip apparatus having a first reflective surface and said second reflective surface which are disposed at an angle proportional to the numerical aperture of the first and second foptical ibers, to yield a light beam with adjacent edges that are parallel to one another, to permit a distance independent delivery reflector-collector reflector separation.

The invention may also comprise a catheter tip apparatus arranged in a catheter for the delivery and collection of an energy signal to permit subsequent computerized analysis of body tissue by the collected signal, comprising an optically transparent sheath enclosed elongated housing having a longitudinal axis of rotation, the housing having a first reflective surface disposed thereon, a second reflective surface disposed on the housing distally of the first reflective surface and in axial alignment therewith, a first light conductive fiber in light coupled communication with the first reflective surface and a second light conductive fiber in light coupled communication with the second reflective surface, the first light conductive fiber in communication being in communication with a controlled analytical-light generating source and the second light conductive fiber being in communication with a light-collection analysis device. A generally curvilinear cover may be arranged to mate over a distal portion of the housing to enclose the reflective surfaces, the cover having at least one opening on an annular surface thereof to permit light delivery to the body tissue, and to permit light collection therethrough upon reflection from the body tissue. At least one of the reflective surfaces may comprise a mirrored member. Each of said light conductive fibers may have a distal end arranged within the housing, and the at least one of the light conductive fibers is in abutting relationship with a non-reflective surface of the mirrored member. At least one of the reflective surfaces may be disposed in a holding pocket. The reflective surface may be secured in the holding pocket by an adhesive. An index matching fluid may be disposed about the reflective surfaces to minimize back reflections thereto, from the outer sheath.

The invention may also comprise a catheter tip apparatus arranged in a catheter for the delivery and collection of an energy signal to permit subsequent computerized analysis of body tissue by the collected signal, comprising an optically transparent sheath enclosed elongated housing having a longitudinal axis of rotation. The housing may have a first reflective light delivery surface disposed thereon and a first reflective light collection surface disposed on the housing distally of the first reflective light delivery surface and in axial alignment therewith. A first light conductive fiber is in light coupled communication with the first reflective light delivery surface and a second light conductive fiber is in light coupled communication with the first reflective light collection surface, the first light conductive fiber in being in communication with a controlled analytical-light generating source and the second light conductive fiber being in communication with a light-collection analysis device, and a second reflective light collection surface may be disposed on the housing distally of the first reflective light collection, the second reflective collection surface may also be in communication with the controlled analytical-light generating source and in axial alignment therewith. The first and second reflective surfaces are thus arranged to permit deep tissue light energy penetration and collection and analysis thereby. Reflectors may otherwise be known as beam redirecting members comprised of aspheric members, planar, spherical, convex surfaces, concave surfaces, comprised of mirrors, dielectric mirrors, refractive index interfaces or diffractive optical elements.

The invention may also include a method of delivering and collecting a tissue-striking light energy signal from a first light fiber and adjacent delivery reflector and returning said light energy signal to a collection reflector adjacent a second light fiber for analysis and tissue treatment. The method includes spacing the collection reflector distally of the delivery reflector in a sheath enclosed elongated catheter housing tip, the housing having a longitudinal axis; disposing the reflectors at an angle with respect to the longitudinal axis of the elongated housing proportional to a numerical aperture of the first and second energy fibers. The method may include bathing the reflectors in an index matching fluid to minimize back reflection in the sheath enclosed housing, and directing the delivery light energy signal and the collection light energy signal so as to yield adjacent edges thereof that are parallel.

Thus what has been shown as a unique arrangement of structures for supporting energy carrying fibers such as flexible optical fibers to permit particular radiation to be delivered from one reflective surface and collected on a second adjacent reflective surface and analyzed in a computer apparatus at the proximal end of those fibers.

BRIEF DESCRIPTION OF THE DRAWINGS

The objects and advantages of the present invention will become more apparent when viewed in conjunction with the following drawings in which:

FIG. 4b is an exploded view of the coil and probe components shown in FIG. 4a;

FIG. 5b is a view similar to FIG. 5a showing the frame components thereof without the surrounding elongated housing;

FIG. 6a is a perspective view of a probe assembly showing a one piece housing arrangement with optical fibers in a counterwound coil;

FIGS. 6b, 6c and 6d are side elevational views of the housing shown in FIG. 6a;

DETAILED DESCRIPTION OF THE PREFERRED EMBODIMENTS

Figure 1:
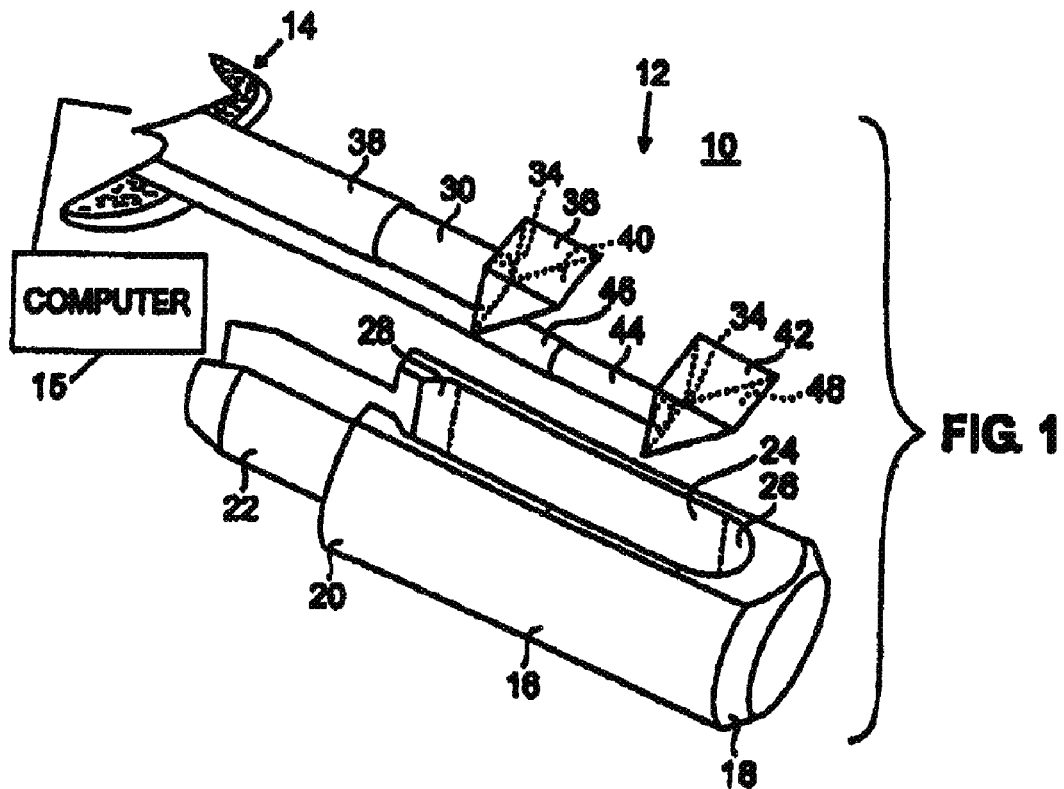
FIG. 1 is an exploded view of a probe housing and an optical fiber arrangement adaptable for insertion into a mammalian body.

Referring now to the drawings in detail, and particularly to FIG. 1, there is shown a first embodiment of the present invention which comprises a catheter tip apparatus 10 and a method of use of that apparatus 10 to provide an analysis of body tissue using an energy spectrum analysis distributed and received by an elongated probe 12 introducable through a catheter sheath 14 into that body tissue. That introduction of the catheter sheath 14 and body probe 12 may be done through an endoscope, or other catheter-like devices, not shown, for such energy diagnosis and treatment of tissue by a proper computer apparatus 15. The energy analysis and treatment might include fluorescence spectroscopy, near infrared (NIR) reflectance spectroscopy, Raman spectroscopy, and optical coherence tomography, photodynamic drug activation, photonic ablation and thermal treatments.

Figure 2:
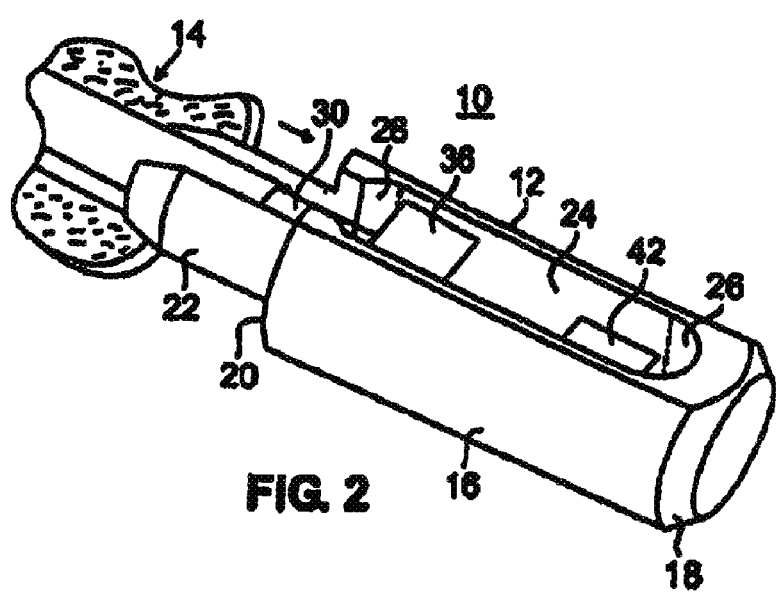
FIG. 2 is a view similar to FIG. 1, showing the fiber components arranged within the elongated housing.

The probe 12 of the present invention comprises an elongated, generally cylindrically shaped housing 16, as shown in FIGS. 1 and 2, having a first or distal end 18 and a second or proximal end 20. The proximal end 20 has a stem 22 thereon of reduced diameter from the diameter of the distalmost 18 portion thereof. An elongated groove 24 is arranged to extend from the proximal end 20 of the stem 22 through towards the distal end 18 of the housing 16, as may be seen in FIGS. 1 and 2. The groove 24 extends only through one side of the housing, and has an arrangement of angled shoulders 26 and 28 therein for providing snug receipt of the collector fiber 30 and the delivery fiber 44.

The collector fiber arrangement in this particular embodiment includes the elongated flexible collection fiber 30 having a distal end 34 to which a reflector or reflective surface 36 (i.e. mirrored/polished member) is attached. The collection fiber 30 has an outer buffer 38, for protection of the fiber and to minimize stray radiation therefrom. The reflector 36 has an angularly disposed reflective surface 40 thereon.

The delivery reflector 42 is attached to an optical delivery fiber 44 which is enclosed similarly by an outer buffer 46 such as a sheath for protection of the fiber and for minimization of light leakage. The delivery reflector 42 has an angled reflective surface 48 thereon. The collection fiber 30 and attached reflector 36 and the delivery fiber 44 and its attached reflector 42 jointly mate within the elongated receiving groove 24 within the stem and tip housing 16. The elongated groove 24 is preferably shaped to effect accurate positioning of the respective reflectors 36 and 42 therein, so as to emit radiation from the delivery reflector 42 and receive radiation reflected back from a body tissue sample through the collection (reflector) 36. Once the collection and delivery fibers 30 and 44 are within the housing 16, those joint fibers 30 and 44 may be inserted within the elongated catheter shaft 14 or rotatable coil as will be described hereinbelow.

Figure 3:
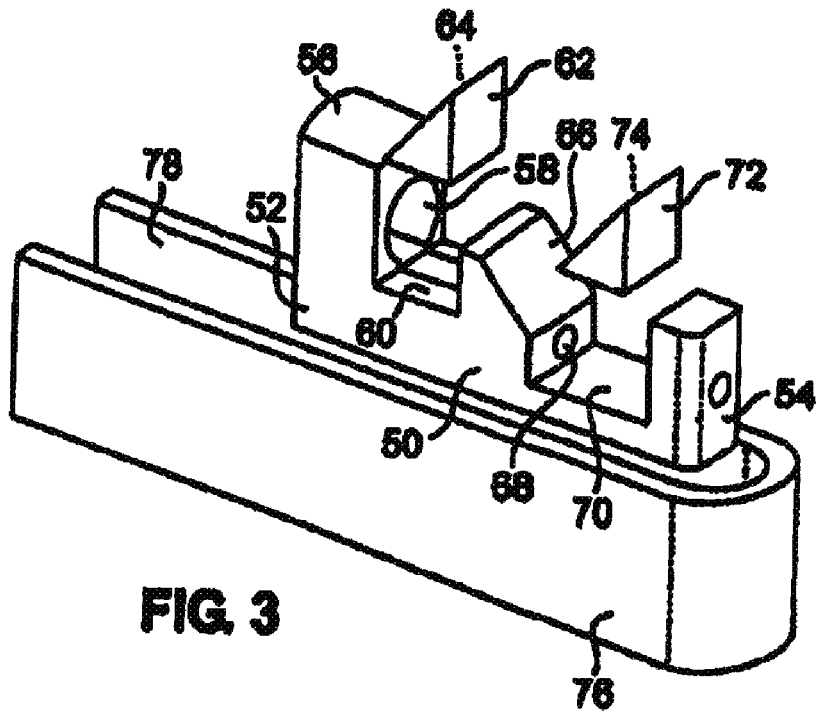
FIG. 3 is an exploded view in perspective, of a prism and support frame arrangement and a housing for that support frame, for attachment on the distal end of a set of optical fibers.

A further embodiment of the present invention shown in FIG. 3 and is disclosed as an elongated support frame 50 having a proximal end 52 and a distal end 54. The proximal end 52 includes an upstanding portion 56 through which a collection fiber support and alignment channel 58 is arranged (i.e. molded, drilled, machined). A rectilinearly-shaped holding pocket 60 is arranged distal of the first upstanding member 56 and is arranged to receive a reflective mirrored surface 62, (for example, a reflective collection member) having a reflecting surface 64 thereon. An upstanding midblock potion 66 is arranged centrally of the support frame 50 and has a delivery fiber support and alignment channel 68 arranged therewithin. The delivery fiber channel 68 extends parallel and adjacent the collection fiber channel 58. A second holding or receiving pocket 70 is similarly arranged distally adjacent the midblock portion 66 for adhesive receipt of a second reflector or mirrored surface (i.e. mirror or reflective member) 72 having a mirrored surface 74 thereon. The holding pockets 60 and 70 are constructed so as to accurately receive and align the respective first and second reflector arrangements (i.e. mirrors or reflective members) 62 and 72 to the desired angle for the desired photon delivery and photon collection from a target body tissue, not shown for clarity. The elongated support frame 50 is arranged within an elongated generally U-shaped housing 76, having an elongated channel 78 for receipt thereof. A delivery fiber and a collection fiber would be inserted within their respective channels 68 and 58 and the respective reflectors (i.e. reflective members/mirrors) 72 and 62 would be secured (i.e. affixed by adhesive) within those respective holding pockets 70 and 60.

Figure 4A:
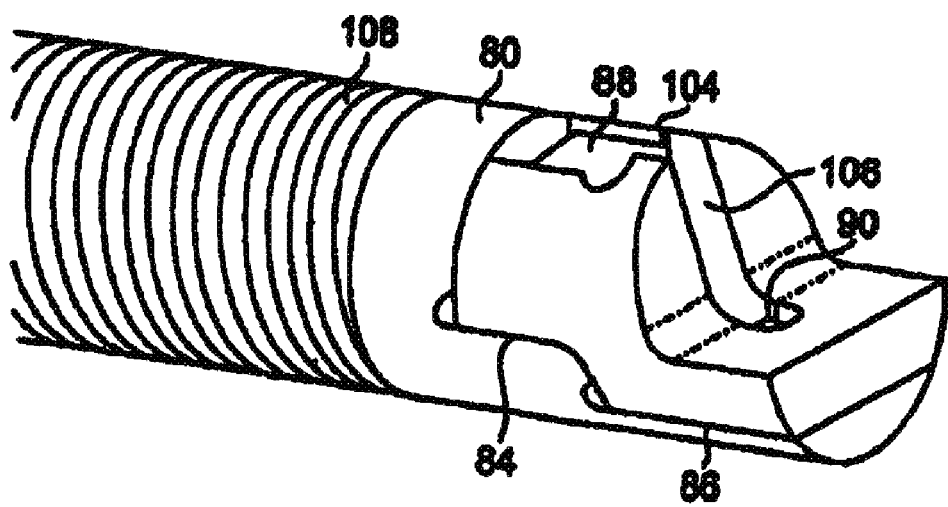
FIG. 4a is a view of a collection and delivery probe arranged on the distal end of a transmission coil in a perspective view thereof.
Figure 4B:
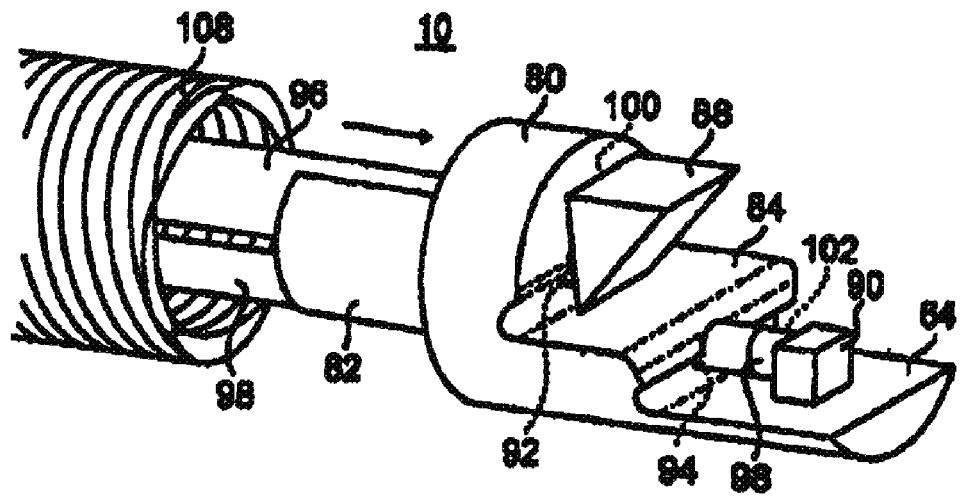

A further embodiment of the optical probe arrangement of the present invention is shown in FIGS. 4(*a*) and 4 (*b*) and is characterized by a generally cylindrically shaped frame member 80 having a stepped down stem portion 82 on its proximal end thereof, as may be seen in FIG. 4(*b*). The frame member 80 is arranged so as to define a series of distal step portions 84 and 86, the first portion 84 of which is arranged to receive a collection reflector (i.e. reflective member or reflective surface) 88 and the second stepped portion 86 receives a delivery reflector (i.e. reflective member or reflective surface) 90. A bore or channel 92 and 94 is arranged through the frame 80 for servicing each particular reflector 88 and 90. Each respective channel 92 and 94 receives a collection fiber 96 or an optical fiber 98 which is arranged to abut a planar surface 100 and 102 of its respective reflector 88 and 90. A distal cover 104 as shown in FIG. 4(*a*) may be arranged so as to mate over the respective collection reflector 88 and delivery reflector 90 while having a slot 106 for passage of a delivered or received photonic signal therethrough. The delivery reflector 90 is thus permitted to emit photonic radiation and the collection prism 88 is permitted to receive photonic radiation when the frame 80 is assembled with the cover 104 and the stem 82 is attached and holding the particular fibers 96 and 98, and those fibers 96 and 98 are inserted within a hollow, torqueable transmission shaft such as a counter wound multifilar drive shaft coil arrangement 108 proximal of that frame member 80 and secured to the stem 82.

Figure 5A:
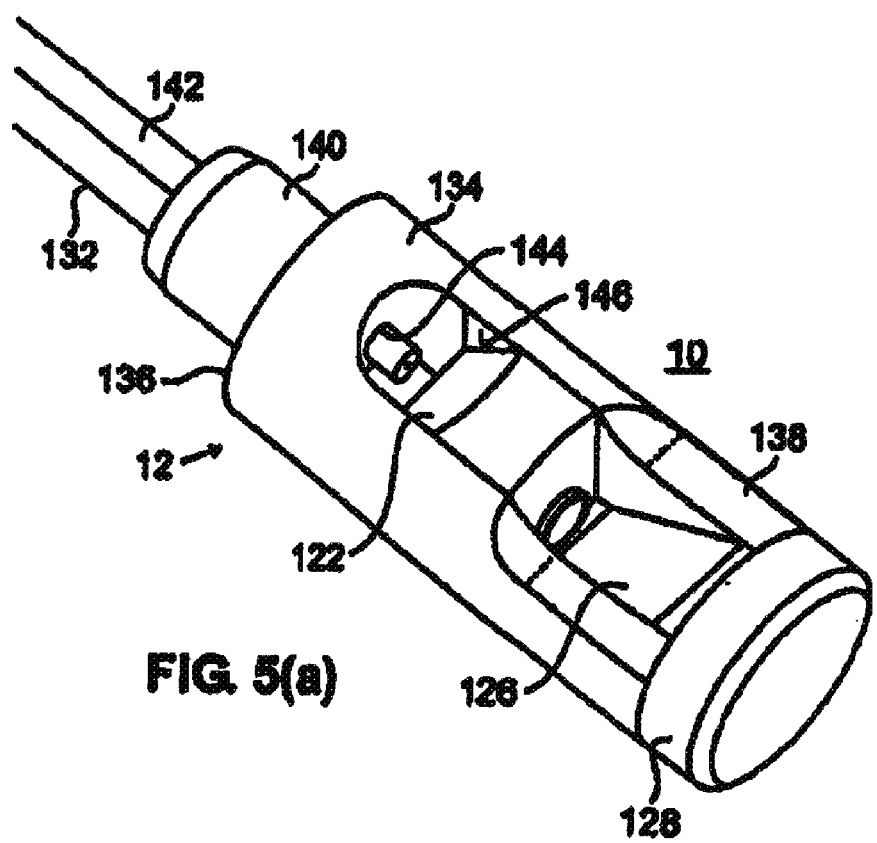
FIG. 5a is a perspective view of an assembly of an elongated housing having a pair of reflective surfaces arranged therewithin.

A further embodiment of the probe arrangement of the present invention is shown in FIGS. 5(*a*) and 5(*b*) by an elongated frame member 116 having a proximal end 118 and a distal end 120, as may be best seen in FIG. 5(*b*). The proximal end 118 of that frame member 116 is arranged so as to define an first angled reflective surface 122 at an upright portion 124 thereof, the distal end 120 of that frame member 116 having a second upright portion 125 with a second reflective surface 126 angularly disposed thereon with an oval end cap 128 thereon. A bore 130 is arranged through the upright portion 124 on the proximal end 118 of the elongated frame member 116 so as to define a receiving channel for a delivery fiber 132 to be inserted therewithin. The entire elongated frame 116 is inserted into an elongated housing 134, as shown in FIG. 5(*a*), having a proximal end 136 and a distal end 138. The proximal end 136 of the housing 134 has a stem 140 with a stepped down diameter which encloses the delivery fiber 132 and a collection fiber 142. The stem 140 of the housing 134 is arranged to receive the collection fiber 142 which is arranged to receive reflective signals from its reflection surface 122 arranged onto the upstanding portion 124 of the elongated frame member 116. The housing 134 has an opening 144 arranged longitudinally therein, as shown in FIG. 5(*a*), so as to receive the elongated frame member 116. The housing 134 also has a slot 146 cut through its side portion thereof so as to permit the photonic energy signal to be delivered and received by the respective reflective surfaces 126 and 122 contained therewithin. The end cap 128 on the distalmost end 120 of the elongated frame member 116 abuts the distalmost end 138 of the elongated housing 134 to define a smooth continuous surface therearound.

Figure 6B:
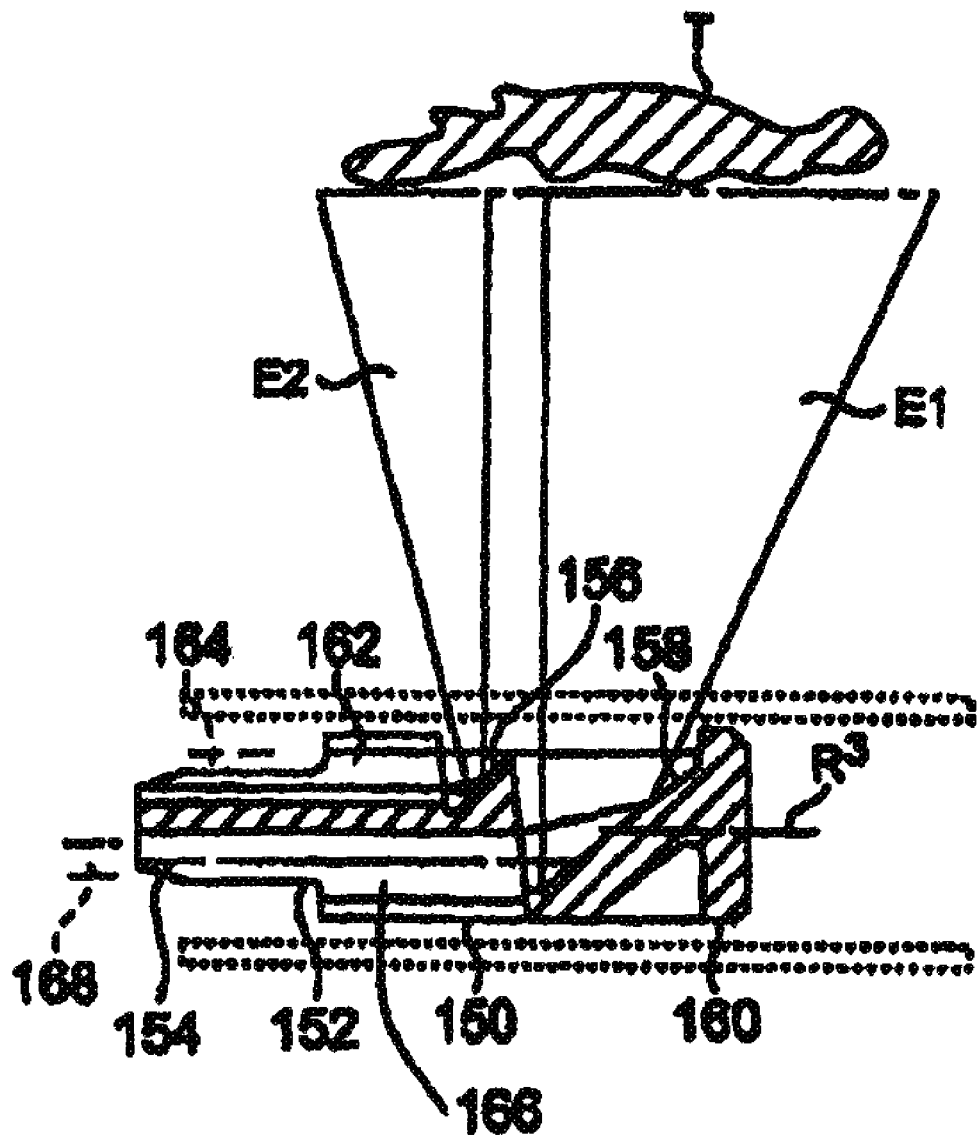
Figure 6C:
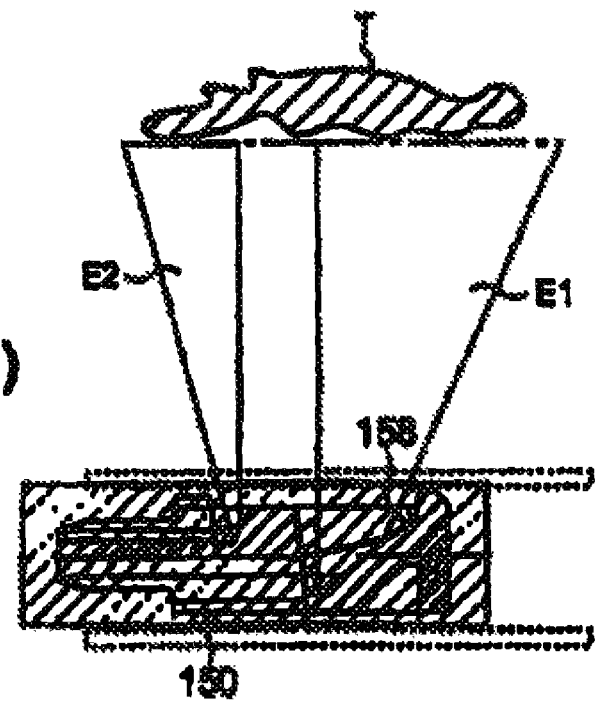
Figure 6D:
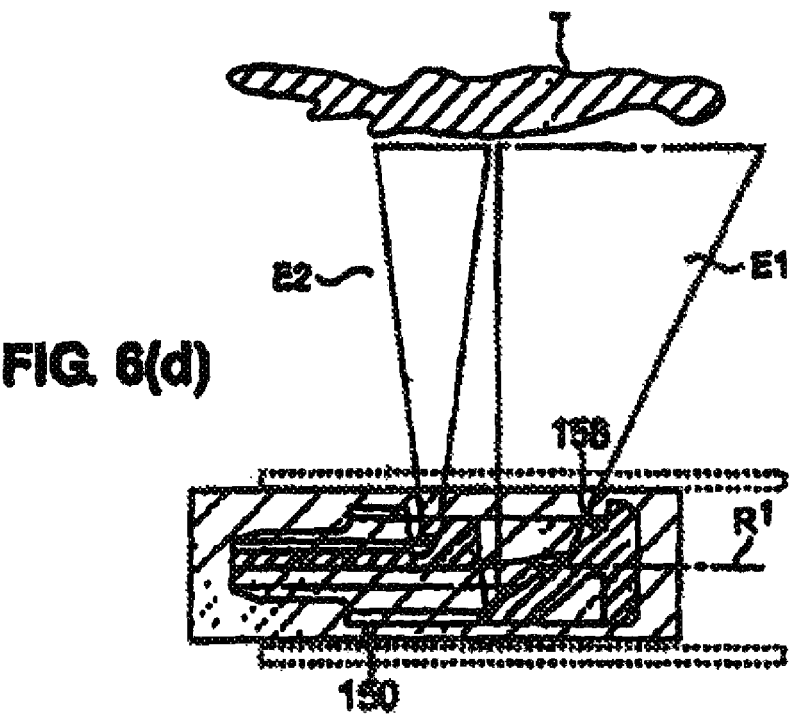

A further embodiment of the present invention resides in a one piece housing 150 of generally cylindrical shape, (as may be seen in FIGS. 6(*a*), 6(*b*), 6(*c*) and 6(*d*)), having a proximal portion 152 of stepped down diameter defining a reduced-diameter fiber-enclosing stem 154. A first reflective collection surface 156 is disposed at a particularly desired angle near the stem 154 of the housing 150, and a second reflective surface 158 is disposed onto the elongated housing 150 adjacent its distalmost end 160. A first channel or bore 162 is arranged through the proximal end 152 of the housing 150 adjacent the stem 154 so as to snugly and alignably receive a signal collection fiber 164. A second channel or bore 166 is also arranged through the proximal half of the elongated housing 150 so as to alignably support a delivery fiber 168 therethrough. The stem 154 may be received in a pair of hollow, flexible, counterwound coils 170, as shown in FIG. 6(*a*), which coils 170 that function as a torqueable transmission shaft, is secured to the stem 154 and surrounds the delivery and collection fibers 168 and 164 received therethrough. The first and second reflective surfaces 156 and 158 arranged into the housing 150, in this embodiment, and which is depicted by light energy waves E1 and E2 reflecting with respect thereto, may be skewed (non parallel or curvilinear) with respect to one another so as to emit and receive signals from any particular direction with respect to the surface of an adjacent reflective tissue "T." FIG. 6(*c*) represents the housing 150 with the respective reflective surfaces 156 and 158 being spaced further longitudinally apart than is depicted in FIG. 6(*b*). This permits different scattering patterns E1 and E2 to be delivered and hence received by the catheter tip apparatus 10. FIGS. 6(*d*) represents the manufactured reflective surfaces 156 and 158 at a skewed angle with respect to one another to present further signal delivery and collection characteristics with respect thereto. The fiber bores 154 and 162 are oppositely aligned and diametrically disposed across the longitudinal axis of rotation "R" of the housing 150. This minimizes eccentric rotation of the housing 150, the fibers borne therein and signal distortion during rotation of the housing 150 in a body vessel during analysis of tissue "T".

Figure 7:
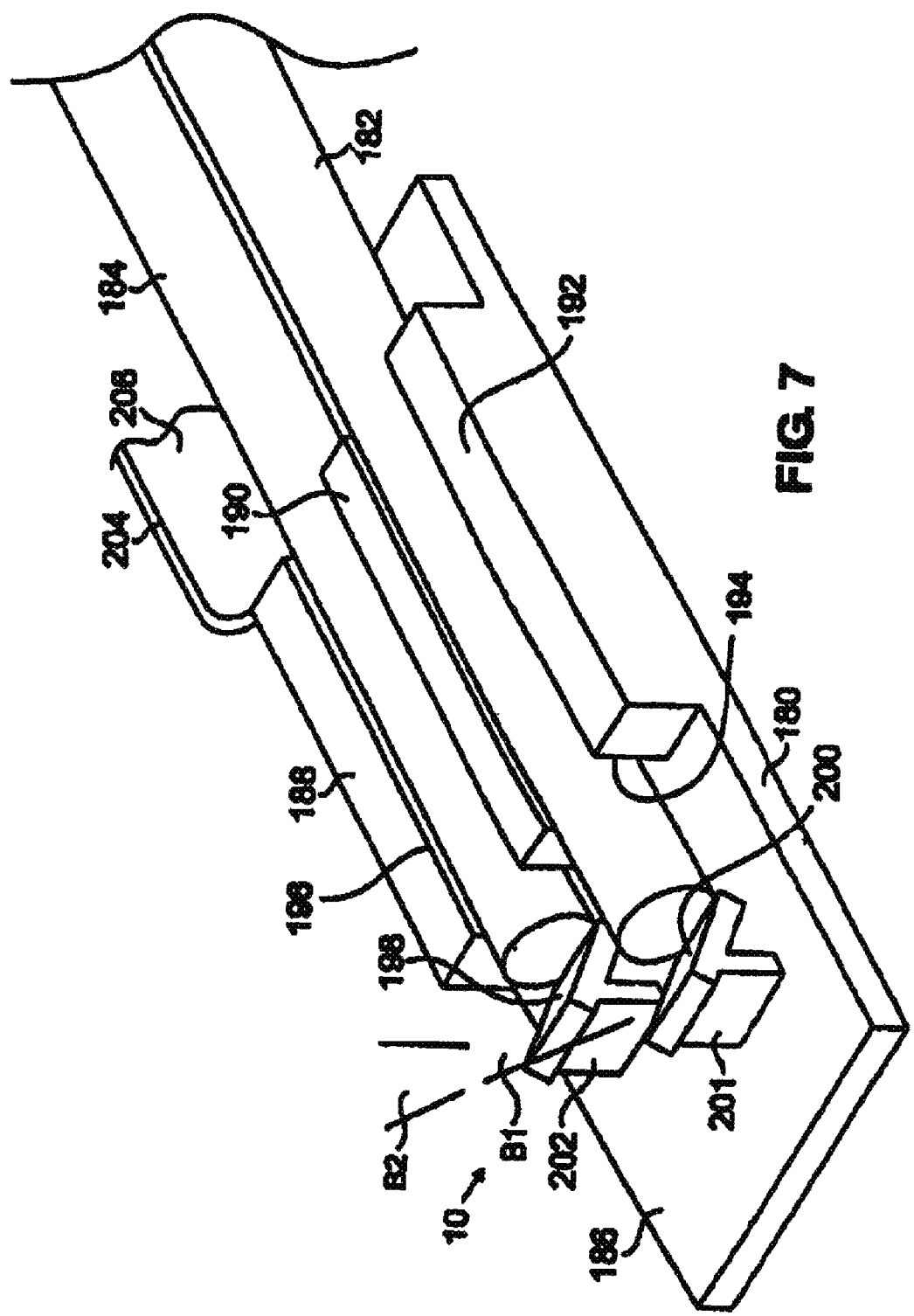
FIG. 7 shows a perspective view of a fiber supporting catheter tip housing arrangement manufactured by additive and subtractive methods.

A yet further embodiment of the present invention is shown in FIG. 7, wherein a platform 180 relates to a method of constructing a catheter tip arrangement 10 for support of a plurality of two or more optical delivery and collection fibers 182 and 184, which "support" construction permits minimization of component size and adaptive angularity of reflection of the delivery and collection beams B1 and B2. Such a support platform 180 may be accomplished by micro-machining construction where additive or subtractive processing such as for example: etching, plating, sputtering, vapor deposition and subtractive processing such as etching, laser cutting and ablation permits finite adjustment to the dimensions. The support platform 180 comprises a base 186 upon which an arrangement of elongated, parallel bosses 188, 190 and 192 are "grown", the bosses 188, 190 and 192 defining between them, a pair of parallel slots 194 and 196 into which a delivery and a collection fiber 182 and 184 may be respectively mated. A mirror surface 198 and 200 and support struts 201 and 202 are spaced at the distalmost location of the fibers 182 and 184, which mirror surfaces 198 and 200 may be curved or manipulably bent to the desired angle for maximizing optical analysis and tissue treatment thereby. This embodiment shown in FIG. 7 contemplates the use of index-matching fluids 206 added to any gap between a catheter sheath 204 surrounding the fibers 182 and 184, to reduce any back reflections from the interior of the protective sheath/transmission window.

Figure 8:
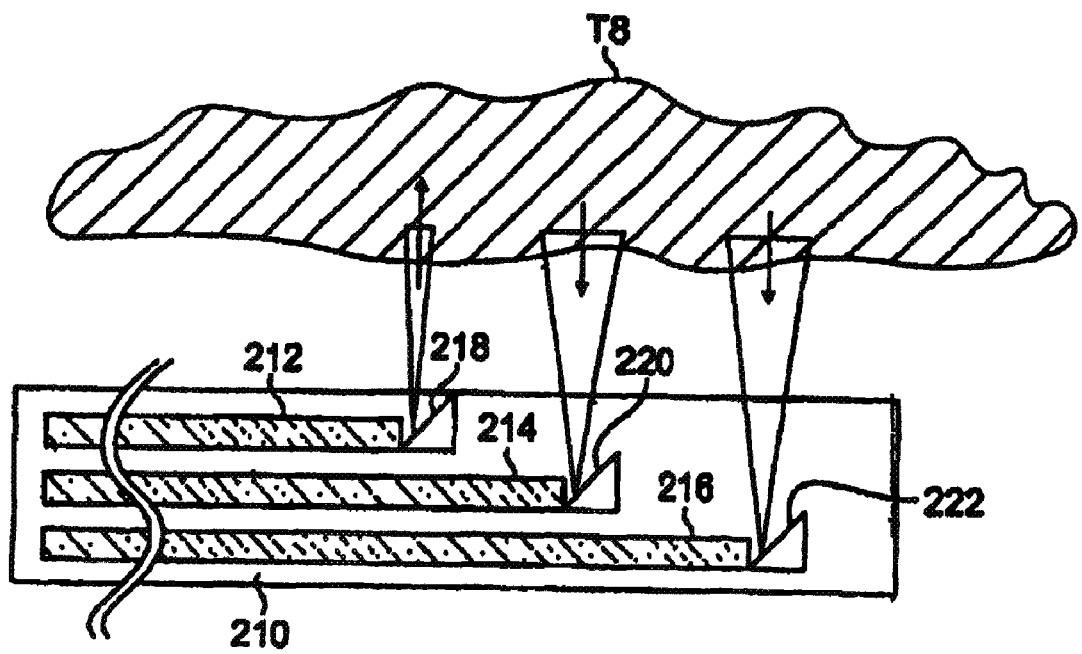
FIG. 8 shows a schematic representation of multiple collection fibers in a housing.

FIG. 8 shows a schematic representation of a catheter tip disposed elongated housing 210 having an optical energy delivery fiber 212 and a first optical energy collection fiber 214 and a second optical energy collection fiber 216 in optical communication with a mammalian tissue "T8". Each fiber 212, 214 and 216 have a reflective surface 218, 220 and 222 disposed distally thereof respectively, as shown in FIG. 8. The reflective surfaces 218, 220 and 222 are axially spaced apart from one another. Multiple collection fibers 214 and 216 with axially spaced apart collection reflective surfaces 220 and 222 permit collection and analysis of light that has penetrated more deeply into the tissue "T8". The reflective surfaces 218, 220 and 222 may be aspheric volumes, or flat, convex, concave or curved members having an arcuate surface to present a straight reflective beam, a spread-out beam, a focused beam which may overlap one another, be parallel to one another, or in alignment with one another. Multiple collectors 220 and 222 permits the receiving or collection of light emitted from a single source but collected from more than one collector arranged at spaced apart locations within the tissue being investigated. The beams may have a delivery numerical aperture NA of between NA=0.1 and NA=0.6 and a collection numerical aperture NA of between NA=0.1 and NA=0.7. Bean redirecting members such as mirrors preferably have separations of about 0.1 mm and 2 mm.

Figure 9A:
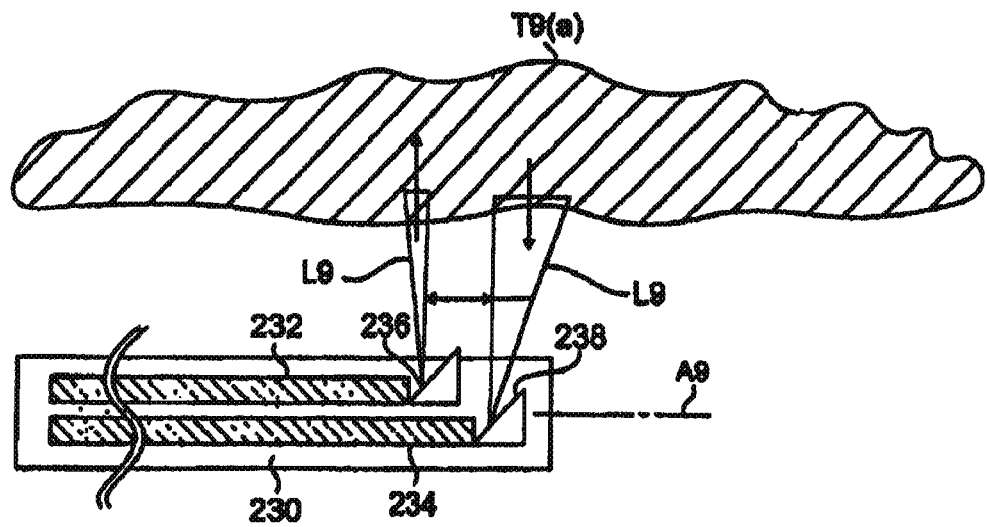
FIGS. 9a and 9b show reflectors arranged in their elongated housing for parallel light reflective beams.
Figure 9B:
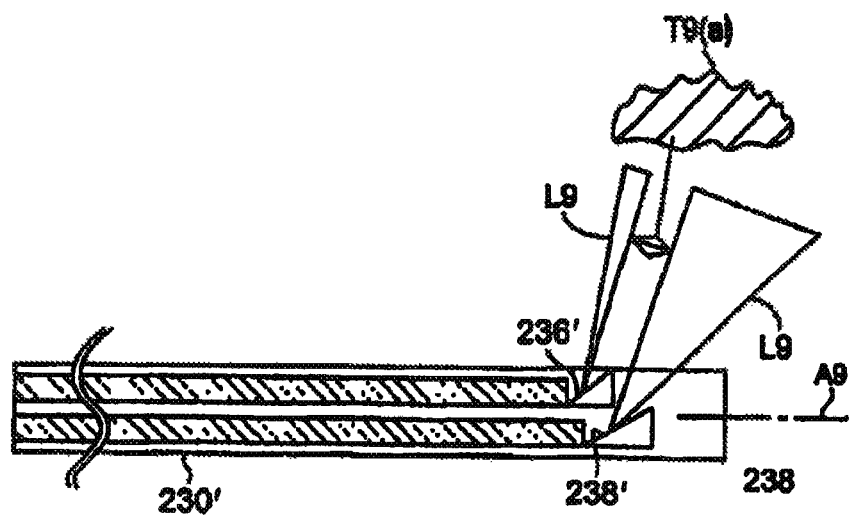

A more preferential delivery and collection beam geometry is shown in FIGS. 9a and 9b having a catheter tip disposed elongated housing 230 having an optical delivery fiber 232 and an optical energy collection fiber 234 in optical communication with mammalian tissue "T9a". A reflective surface 236 delivers a generally radially delivered light beam L9 and a reflective surface 238 collects the generally radially directed returning light beam L9. Adjacent portions of the delivered beam and the returning beam in this embodiment are parallel, because the delivery and collection reflectors 236 and 238 are disposed at chosen angles proportional to the numerical aperture of the delivery and collection fibers 232 and 234 to yield energy beam having edges that are parallel to permit distance independent delivery-collector separation, and angularity of the reflectors 236' and 238' being shown at a less steep angle with respect to the longitudinal axis A9, in an elongated housing 230', represented in FIG. 9b. It is also contemplated that each fiber may be utilized for both delivery and collection of light energy.

Thus what has been shown as a unique arrangement of structures for supporting energy carrying fibers or waveguide elements to permit particular radiation to be delivered from at least one beam redirecting member such as a reflective surface and collected on the same or at least a second adjacent beam redirecting member such as a second reflective surface and analyzed in a light signal analyzer computer apparatus connected to the proximal end of those fibers, waveguides or beam bearing members.

The invention claimed is:

1. A catheter tip apparatus, comprising:
    an elongated housing rotatably supported on a flexible shaft, wherein said housing comprises a member having first and second reflective surfaces integral therewith, said first reflective surface and second reflective surfaces being longitudinally spaced apart from one another;
    a delivery fiber comprising a first fiber having a distal end adjacent to the first reflective surface; and
    a collection fiber comprising a second fiber having a distal end adjacent to the second reflective surface;
    wherein said second reflective surface is larger than said first reflective surface and said collection fiber has a greater diameter than said delivery fiber.

2. The catheter tip apparatus of claim 1, wherein said first reflective surface and said second reflective surface are not parallel to one another.

3. The catheter tip apparatus of claim 2, wherein said first and second reflective surfaces are arranged to cause respective fields of view of said delivery and collection fibers to be non-intersecting.

4. The catheter tip apparatus of claim 1, wherein one of said first and second reflective surfaces is curvilinear.

5. The catheter tip apparatus of claim 1, wherein said delivery and collection fibers are diametrically disposed about a longitudinal axis of rotation of said housing.

6. The catheter tip apparatus of claim 1 wherein said first reflective surface is disposed radially within and spaced from the perimeter of said housing.

7. A catheter tip apparatus, comprising:
    an elongated housing rotatably supported on a flexible shaft, wherein said housing comprises a member having first and second reflective surfaces integral therewith, said first reflective surface and second reflective surfaces being longitudinally spaced apart from one another;
    a first fiber having a distal end adjacent to the first reflective surface; and
    a second fiber having a distal end adjacent to the second reflective surface;
    wherein said second reflective surface is larger than said first reflective surface and the housing member is a single member of generally cylindrical shape having a proximal portion of stepped-down diameter defining a reduced-diameter stem.

8. The catheter tip apparatus of claim 7, wherein a first channel is arranged through the proximal end of the housing adjacent to the stem and said first channel supports said first fiber.

9. The catheter tip apparatus of claim 8, wherein a second channel is arranged through the proximal end of the housing adjacent to the stem and said second channel supports said second fiber.

10. The catheter tip apparatus of claim 7, wherein both the first and second fibers are capable of delivery and collection of light energy signals.

* * * * *